United States Patent
Korfhage et al.

(10) Patent No.: US 11,085,073 B2
(45) Date of Patent: Aug. 10, 2021

(54) METHOD FOR IMMOBILIZING A NUCLEIC ACID MOLECULE ON A SOLID SUPPORT

(71) Applicant: QIAGEN GmbH, Hilden (DE)

(72) Inventors: Christian Korfhage, Hilden (DE); Evelyn Fricke, Hilden (DE)

(73) Assignee: QIAGEN GmbH, Hilden (DE)

( * ) Notice: Subject to any disclaimer, the term of this patent is extended or adjusted under 35 U.S.C. 154(b) by 435 days.

(21) Appl. No.: 15/567,504

(22) PCT Filed: Apr. 25, 2016

(86) PCT No.: PCT/EP2016/059171
§ 371 (c)(1),
(2) Date: Oct. 18, 2017

(87) PCT Pub. No.: WO2016/170182
PCT Pub. Date: Oct. 27, 2016

(65) Prior Publication Data
US 2018/0105871 A1    Apr. 19, 2018

(30) Foreign Application Priority Data
Apr. 24, 2015  (EP) .................................. 15164958

(51) Int. Cl.
| C12P 19/34 | (2006.01) |
| C12Q 1/6834 | (2018.01) |
| C12Q 1/6806 | (2018.01) |
| C12Q 1/6837 | (2018.01) |
| C12Q 1/6844 | (2018.01) |

(52) U.S. Cl.
CPC ......... *C12Q 1/6834* (2013.01); *C12Q 1/6806* (2013.01); *C12Q 1/6837* (2013.01); *C12Q 1/6844* (2013.01); *C12Q 1/6846* (2013.01)

(58) Field of Classification Search
USPC ....... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS

| 5,641,658 A | 6/1997 | Adams et al. |
| 5,700,642 A | 12/1997 | Monforte et al. |
| 6,300,070 B1 | 10/2001 | Boles et al. |
| 7,115,400 B1 | 10/2006 | Adessi et al. |
| 7,790,418 B2 | 9/2010 | Mayer |
| 7,972,820 B2 | 7/2011 | Mayer |
| 9,360,526 B2 | 6/2016 | Vogelstein et al. |

(Continued)

FOREIGN PATENT DOCUMENTS

| WO | 2013/028643 A1 | 2/2013 |
| WO | 2014/020154 A1 | 2/2014 |
| WO | 2014/026031 A1 | 2/2014 |

OTHER PUBLICATIONS

"DNA glycosylase" from Wikipedia. Printed on Aug. 30, 2020.*
(Continued)

*Primary Examiner* — Frank W Lu
(74) *Attorney, Agent, or Firm* — Seed IP Law Group LLP

(57) ABSTRACT

The present invention is directed to a method for immobilizing a nucleic acid molecule on a solid support and to a use of a combination of a first nucleic acid immobilized primer linked to a solid support and a second immobilized primer linked to said solid support in said method.

Figure 1:
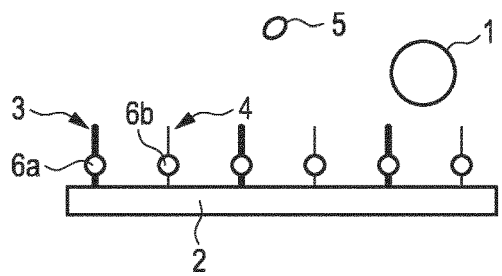
Figure 1:
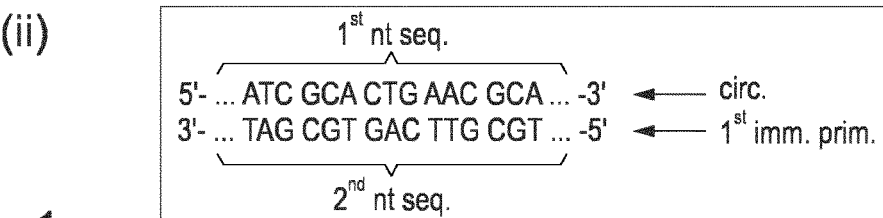
Figure 1:
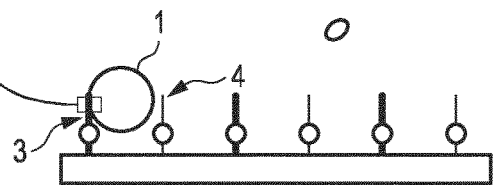
Figure 1:
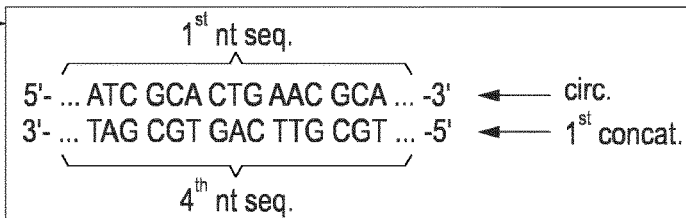
Figure 1:
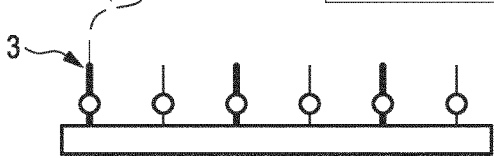
Figure 1:
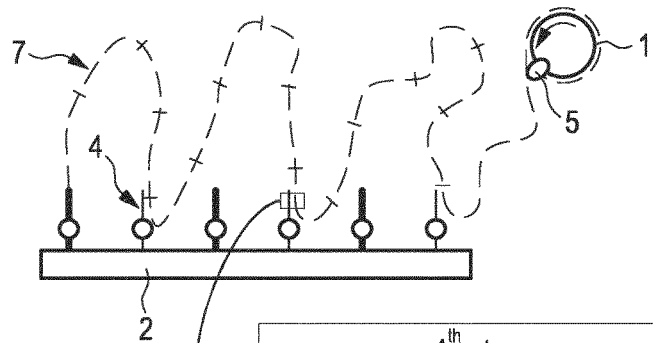
Figure 1:
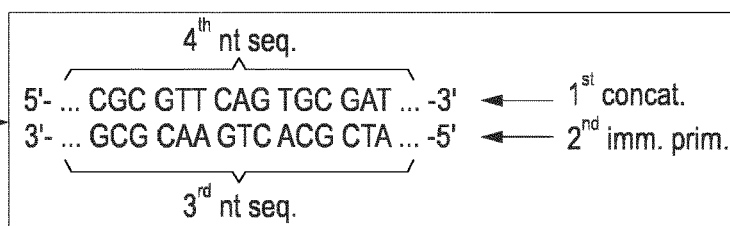
Figure 1:
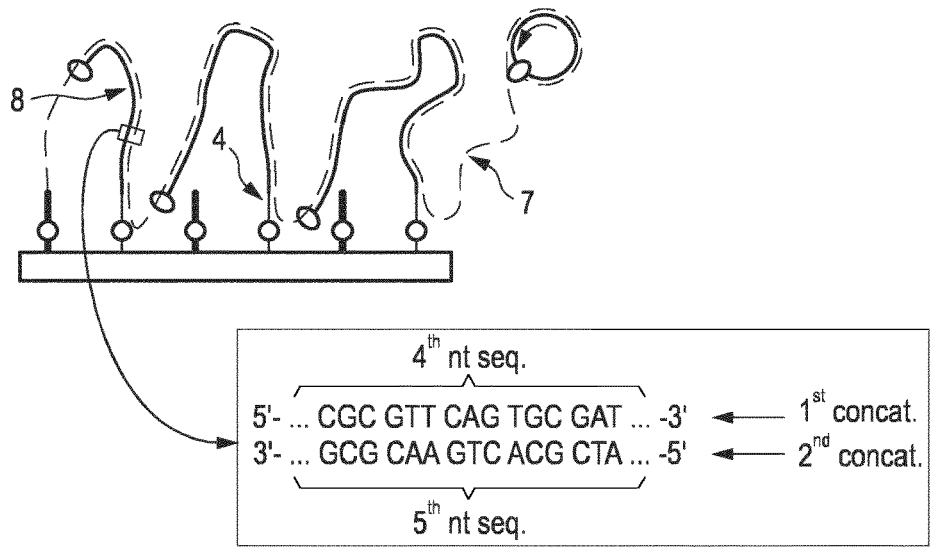
Figure 1:
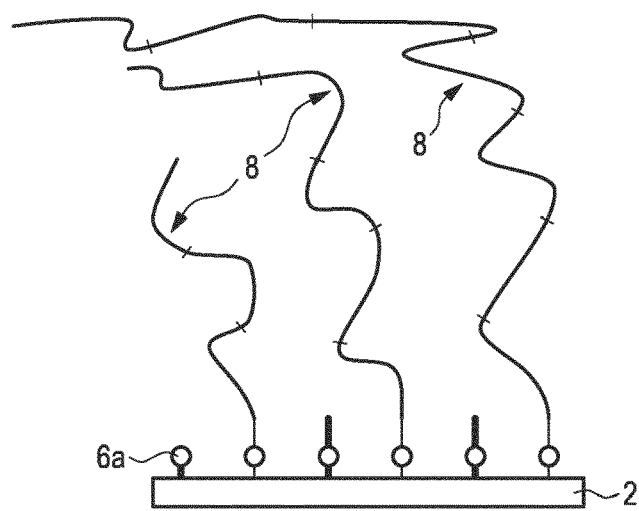
Figure 1:
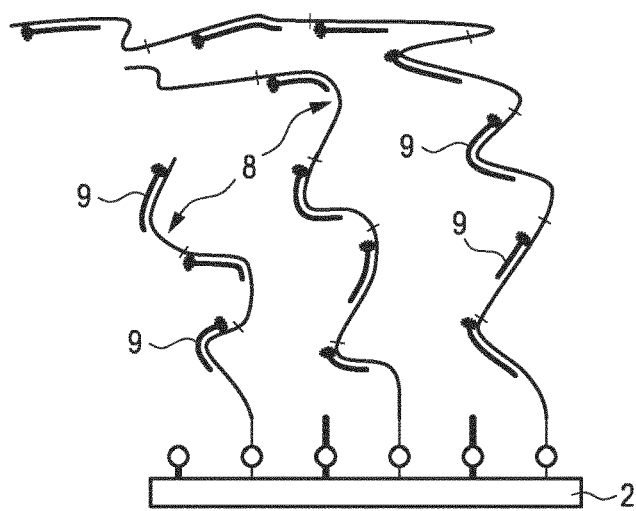

15 Claims, 4 Drawing Sheets
Specification includes a Sequence Listing.

(56) References Cited

U.S. PATENT DOCUMENTS

| | | | |
|---|---|---|---|
| 2002/0012933 | A1 | 1/2002 | Rothberg et al. |
| 2002/0150899 | A1 | 10/2002 | Fu et al. |
| 2003/0148344 | A1 | 8/2003 | Rothberg et al. |
| 2004/0132061 | A1 | 7/2004 | Quinn et al. |
| 2004/0152212 | A1 | 8/2004 | Huang |
| 2007/0190548 | A1 | 8/2007 | Lee et al. |
| 2008/0160580 | A1* | 7/2008 | Adessi ............... C12Q 1/6837 435/91.1 |
| 2009/0018024 | A1 | 1/2009 | Church et al. |
| 2009/0156412 | A1 | 6/2009 | Boyce, IV et al. |
| 2010/0008939 | A1 | 1/2010 | Nelson et al. |
| 2010/0022412 | A1 | 1/2010 | Rigatti et al. |
| 2010/0075328 | A1 | 3/2010 | Bjornson et al. |
| 2010/0316998 | A1 | 12/2010 | Gefter |
| 2011/0195457 | A1 | 8/2011 | Nelson et al. |
| 2012/0156728 | A1 | 6/2012 | Li et al. |
| 2012/0178638 | A1 | 7/2012 | Damha et al. |
| 2012/0289426 | A1 | 11/2012 | Roos et al. |
| 2013/0296172 | A1 | 11/2013 | Fu et al. |
| 2015/0045254 | A1 | 2/2015 | Jack |
| 2017/0204459 | A1* | 7/2017 | Barany ............... C12Q 1/6816 |

OTHER PUBLICATIONS

AlkD from Wikipedia. Printed on Aug. 30, 2020.*

"Multiple displacement amplification" from Wikipedia. Printed on Aug. 30, 2020.*

Malhotra et al., "Molecular Methods in Microbiology and their Clinical Application," *Journal of Molecular and Genetic Medicine* 8(4):1000142 (9 pages) (2014).

Adessi et al., "Solid phase DNA amplification: characterisation of primer attachment and amplification mechanisms," *Nucleic Acids Res.* 28(20):e87 (8 pages) (2000).

Barbee et al., "Fabrication of DNA polymer brush arrays by destructive micropatterning and rolling-circle amplification," *Macromol. Biosci.* 11(5):607-617, 2011. (20 pages).

Bentley et al., "Accurate whole human genome sequencing using reversible terminator chemistry," *Nature* 456(7218):53-59, 2008. (21 pages).

Bronner et al., "Improved Protocols for Illumina Sequencing," *Current Protocols in Human Genetics* 80:18.2.1-18.2.42 (Jan. 23, 2014).

Dean et al., "Rapid amplification of plasmid and phage DNA using Phi29 DNA polymerase and multiply-primed rolling circle amplification," *Genome Research* 11(6):1095-1099 (2001).

Gao et al., "Secondary structure effects on DNA hybridization kinetics: a solution versus surface comparison," *Nucleic Acids Res.* 34(11):3370-3377 (2006).

Ju et al., "Four-color DNA sequencing by synthesis using cleavable fluorescent nucleotide reversible terminators," *Proc. Natl. Acad. Sci. USA* 103(52):19635-19640 (2006).

Lane et al., "Amplicon secondary structure prevents target hybridization to oligonucleotide microarrays," *Biosensors and Bioelectronics* 20(4):728-735 (2004).

Nallur et al., "Signal amplification by rolling circle amplification on DNA microarrays," *Nucleic Acids Res.* 29(23):e118 (9 pages) (2001).

New England Biolabs, "9°$N_m$™ DNA Polymerase," https://www.neb.com/products/m0260-9nm-dna-polymerase, Retrieved from the Internet Nov. 3, 2013, 3 pages.

Sekar et al., "Comparative study of sequence-dependent hybridization kinetics in solution and on microspheres," *Nucleic Acids Res.* 33(1):366-375 (2005).

Yi et al., "Molecular Zipper: a fluorescent probe for real-time isothermal DNA amplification," *Nucleic Acids Res.* 34(11):e81 (5 pages) (2006).

Zhao et al., "Massively parallel display of genomic DNA fragments by rolling-circle amplification and strand displacement amplification on chip," *Talanta* 82(2):477-482 (Jul. 15, 2010).

\* cited by examiner (i)

(ii)

1.

2.

3.

(iii)

(iv)

(v)

A

B

SEQUENCE LISTING

<160> NUMBER OF SEQ ID NOS: 19

<210> SEQ ID NO 1
<211> LENGTH: 34
<212> TYPE: DNA
<213> ORGANISM: Artificial Sequence
<220> FEATURE:
<223> OTHER INFORMATION: Primer 1 forward

<400> SEQUENCE: 1
aaaaaaaatt gcacctatcc ttgcgcagct cgag         34

```
<210> SEQ ID NO 2
<211> LENGTH: 33
<212> TYPE: DNA
<213> ORGANISM: Artificial Sequence
<220> FEATURE:
<223> OTHER INFORMATION: Primer 1 reverse

<400> SEQUENCE: 2
aaaaaaaacc atgaacaaaa tgtgactcat atc                          33

<210> SEQ ID NO 3
<211> LENGTH: 10
<212> TYPE: DNA
<213> ORGANISM: Artificial Sequence
<220> FEATURE:
<223> OTHER INFORMATION: Primer poly A

<400> SEQUENCE: 3
aaaaaaaaaa                                                    10

<210> SEQ ID NO 4
<211> LENGTH: 101
<212> TYPE: DNA
<213> ORGANISM: Artificial Sequence
<220> FEATURE:
<223> OTHER INFORMATION: DNA circle

<400> SEQUENCE: 4
atgacgatat gagtcacatt ttgttcatgg gcatgacatt gatacacagt tagacgatag    60
gacagtacat tcgacctatc cttgcgcagc tcgagatgac g                      101

<210> SEQ ID NO 5
<211> LENGTH: 20
<212> TYPE: DNA
<213> ORGANISM: Artificial Sequence
<220> FEATURE:
<223> OTHER INFORMATION: Primer 2 forward

<400> SEQUENCE: 5
ctgtgtatca atgtcatgcc                                         20

<210> SEQ ID NO 6
<211> LENGTH: 21
<212> TYPE: DNA
<213> ORGANISM: Artificial Sequence
<220> FEATURE:
<223> OTHER INFORMATION: Primer 2 reverse

<400> SEQUENCE: 6
gttagacgat aggacagtac a                                       21

<210> SEQ ID NO 7
<211> LENGTH: 28
<212> TYPE: DNA
<213> ORGANISM: Artificial Sequence
<220> FEATURE:
<223> OTHER INFORMATION: Primer 3 forward

<400> SEQUENCE: 7
tgggcatgac attgatacac agttagac                                28

<210> SEQ ID NO 8
<211> LENGTH: 28
<212> TYPE: DNA
<213> ORGANISM: Artificial Sequence
<220> FEATURE:
```

```
<223> OTHER INFORMATION: Primer 3 reverse

<400> SEQUENCE: 8
aaggataggt cgaatgtact gtcctatc                                              28

<210> SEQ ID NO 9
<211> LENGTH: 47
<212> TYPE: DNA
<213> ORGANISM: Artificial Sequence
<220> FEATURE:
<223> OTHER INFORMATION: Combined DNA/RNA molecule, primer 1 forward

<400> SEQUENCE: 9
aaaaaaaaaa aaaaaaaaaa aaauucgacc uauccuugcg cagcucg                         47

<210> SEQ ID NO 10
<211> LENGTH: 46
<212> TYPE: DNA
<213> ORGANISM: Artificial Sequence
<220> FEATURE:
<223> OTHER INFORMATION: Combined DNA/RNA molecule, primer 1 reverse

<400> SEQUENCE: 10
aaaaaaaaaa aaaaaaaaaa aaaccaugaa caaaauguga cucaua                          46

<210> SEQ ID NO 11
<211> LENGTH: 101
<212> TYPE: DNA
<213> ORGANISM: Artificial Sequence
<220> FEATURE:
<223> OTHER INFORMATION: Non-hybridized circular DNA molecule

<400> SEQUENCE: 11
atgacgatat gagtcacatt ttgttcatgg gcatgacatt gatacacagt tagacgatag           60
gacagtacat tcgacctatc cttgcgcagc tcgagatgac g                              101

<210> SEQ ID NO 12
<211> LENGTH: 40
<212> TYPE: DNA
<213> ORGANISM: Artificial Sequence
<220> FEATURE:
<223> OTHER INFORMATION: Sequencing primer

<400> SEQUENCE: 12
aggcatgtgg ttagacgata ggacagtaca ttcgacctat                                 40

<210> SEQ ID NO 13
<211> LENGTH: 20
<212> TYPE: DNA
<213> ORGANISM: Artificial Sequence
<220> FEATURE:
<223> OTHER INFORMATION: Determined sequence

<400> SEQUENCE: 13
ccttgcgcag ctcgagatga                                                       20

<210> SEQ ID NO 14
<211> LENGTH: 39
<212> TYPE: DNA
<213> ORGANISM: Artificial Sequence
<220> FEATURE:
<223> OTHER INFORMATION: Sequencing primer

<400> SEQUENCE: 14
aggcatgtgc tgtgtatcaa tgtcatgccc atgaacaaa                                  39
```

```
<210> SEQ ID NO 15
<211> LENGTH: 21
<212> TYPE: DNA
<213> ORGANISM: Artificial Sequence
<220> FEATURE:
<223> OTHER INFORMATION: Determined sequence

<400> SEQUENCE: 15
atgtgactca tatcgtcatc g                                             21

<210> SEQ ID NO 16
<211> LENGTH: 15
<212> TYPE: DNA
<213> ORGANISM: Artificial Sequence
<220> FEATURE:
<223> OTHER INFORMATION: Synthetic sequence

<400> SEQUENCE: 16
atcgcactga acgca                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic sequence

<400> SEQUENCE: 17
tgcgttcagt gcgat                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic sequence

<400> SEQUENCE: 18
cgcgttcagt gcgat                                                    15

<210> SEQ ID NO 19
<211> LENGTH: 15
<212> TYPE: DNA
<213> ORGANISM: Artificial Sequence
<220> FEATURE:
<223> OTHER INFORMATION: Synthetic sequence

<400> SEQUENCE: 19
atcgcactga acgcg                                                    15
```

METHOD FOR IMMOBILIZING A NUCLEIC ACID MOLECULE ON A SOLID SUPPORT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_478USPC_SEQUENCE_LISTING. The text file is 4.0 KB, was created on Oct. 28, 2020, and is being submitted electronically via EFS-Web.

The present invention is directed to a method for immobilizing a nucleic acid molecule on a solid support and to a use of a combination of a first nucleic acid immobilized primer linked to a solid support and a second immobilized primer linked to said solid support in said method.

FIELD OF THE INVENTION

The present invention relates to the field of molecular biology, more particularly to the immobilization of nucleic acid molecules to solid supports.

BACKGROUND OF THE INVENTION

In the field of molecular or recombinant biology for many tasks it is necessary to immobilize a large number of DNA molecules on surfaces.

One prominent example requiring large numbers of DNA molecules immobilized on surfaces are high simultaneous or massive parallel sequencing proceedings. There, for the immobilization at first a DNA library is produced. For this purpose, DNA, such as genomic or cDNA, is cut into small linear fragments. The DNA fragments are provided at their ends with adaptor sequences. The central section located between the adapter sequences comprises the DNA which is used for the DNA library preparation. Among all fragments the central sections ideally have low sequence length variability. The actual length of the sequence of the central section depends on the application. For example, for massive parallel sequencing proceedings a length of approximately 200 to 500 bp is preferred. In other applications different lengths may be used.

The DNA fragments of the DNA library are hybridized via at least one of the adaptor sequences to oligonucleotides which were immobilized on a surface. The spacing between the individual hybridization locations can have a random distribution or may be determined via a gridded surface or beads. However, since the individual DNA fragments need to be amplified on the surface the spacing must be as such that after the amplification the individual discrimination remains possible.

In order to produce a sufficiently high number of copies of the DNA fragments to allow a detection or the sequencing on a small panel element, e.g. of a diameter of 1 μm, an amplification of the sequence is carried out.

There are different methods available for the amplification of the individual DNA fragments immobilized on the solid support. These include the method of the so-called bridge amplification as disclosed in U.S. Pat. No. 5,641,658, U.S. Pat. No. 6,300,070, U.S. Pat. No. 7,115,400, U.S. Pat. No. 7,790,418, U.S. Pat. No. 7,972,820, and Adessi et al. (2000), Solid Phase DNA amplification: characterization of primer attachment and amplification mechanism, Nucleic Acids Res. 2000 Oct. 15 28(20):E87. Another method is the so-called Wildfire Amplification as disclosed in US 2012/0156,728. Among these methods is the so-called Rolling Circle Amplification, as disclosed in US 2002/0012933, US 2003/0148344, Barbee et al. (2011), Fabrication of DNA Polymer Brush Arrays by Destructive Micropatterning and Rolling-Circle Amplification, Macromol. Biosci. 2011 12, 11(5):607-17, and Nallur et al. (2001), Signal amplification by rolling circle amplification on DNA microarrays, Nucleic Acids Res. 2001, 29(23):E118.

WO 2014/026031 discloses a method for increasing the sensitivity of high throughput sequencing.

US 2013/0296172 discloses a method for sequencing a target nucleic acid on a surface.

However, the existing methods used for immobilizing and amplifying nucleic acid molecules on a solid support are characterized by complex procedural steps, high error susceptibility and, thus, by a low effectiveness and practicability.

Against this background, it is an object of the present invention to provide a method for immobilizing a nucleic acid molecule on a solid support which allows its amplification on the solid support, and which reduces or avoids the problems associated with the prior art methods.

The present invention satisfies these and other needs.

SUMMARY OF THE INVENTION

The present invention provides a method for immobilizing a nucleic acid molecule on a solid support, comprising:
i) providing a reaction mixture comprising:
    at least one circular nucleic acid template having a first nucleotide target sequence;
    a solid support comprising
        at least one first nucleic acid immobilized primer linked to said solid support and having a second nucleotide sequence being complementary to at least a segment of said first nucleotide target sequence, and
        at least one second nucleic acid immobilized primer linked to said solid support and having a third nucleotide sequence being identical to at least a segment of said first nucleotide target sequence;
    at least one strand displacement polymerase;
    deoxynucleoside triphosphates (NTPs);
    reaction buffer;
ii) incubating said reaction mixture under conditions allowing
    said at least one circular nucleic acid template to anneal to said at least one first nucleic acid immobilized primer;
    said strand displacement polymerase to synthesize at least one first nucleic acid concatemeric amplification product by extending said at least one first nucleic acid immobilized primer by rolling circle amplification (RCA), said at least one first nucleic acid concatemeric amplification product comprises multiple copies of a fourth nucleotide sequence in a head-to-tail orientation, said fourth nucleotide sequence being complementary to at least a segment of said third nucleotide sequence;
    said at least one first nucleic acid concatemeric amplification product to anneal to said at least one second nucleic acid immobilized primer to obtain at least one first nucleic acid concatemeric amplification product-second nucleic acid immobilized primer complex immobilized to said solid support; and iii) incubating said at least one first nucleic acid concatemeric amplification product-second nucleic acid immobilized primer complex allowing said strand displacement polymerase to synthesize at least one second nucleic acid concatemeric amplification product by extending said second nucleic acid immobilized primer by multiple displacement amplification (MDA), said at least one second nucleic acid concatemeric amplification product comprises multiple copies of a fifth nucleotide sequence in a head-to-tail orientation, said fifth nucleotide sequence being complementary to at least a segment of said fourth nucleotide sequence.

The inventors have developed a new method for immobilizing a nucleic acid molecule on a solid support which involves rolling circle amplification (RCA) and which has numerous advantages over the currently used methods in the art.

As used herein, "immobilizing" or "immobilization" refers to a fixing in place of said nucleic acid molecule, in particular to said solid support or its surface, respectively. Said fixing is realized e.g. by a hybridization reaction between two nucleic acid molecules comprising nucleotide sequences being at least partially complimentary to each other, thereby forming a duplex, by a streptavidin-biotin interaction, a covalent bond or a strong ionic bond.

As used herein, a "nucleic acid" or "nucleic acid molecule" may be generally either DNA or RNA, single- or double-stranded, linear or circular, unless specified otherwise.

As used herein, "circular nucleic acid template" refers to a nucleic acid molecule without any free 3' and/or 5' termini or to a nucleic acid molecule where the 3' and 5' intramolecular termini were previously covalently linked to each other, thereby conferring the nucleic acid template a ring- or loop-like or similar structure. The term "template" indicates that the circular nucleic acid molecule encodes a nucleotide target sequence intended to be immobilized to the solid support. The circular nucleic acid template is present in the reaction mixture in a mobile and non-immobilized form.

The circular nucleic acid template can either be artificially produced or may be a naturally occurring DNA. Artificially produced circles are circular nucleic acid molecules which were manipulated or produced by in vitro, e.g. by involving the activities of ligases, polymerases, nucleases etc. Nucleic acid circles can also be isolated or purified from nature, i.e. organisms or the environment, e.g. soil, water, air etc. Common methods for the isolation of naturally occurring circular nucleic acid molecules are well-known to the skilled person. The circular nucleic acid template can be subjected to the reaction mixture either directly after synthesis or isolation or after it has been purified. The purification can comprise one or several steps of physically, chemically, enzymatically or another type.

As used herein, the term "nucleotide" refers to the monomers, or subunits, of nucleic acids like DNA and RNA. Nucleotide may be synonymously used for nucleoside or nucleoside (mono-, di-, tri-) phosphate, and includes the deoxyribose derivatives, i.e. the dNTPs.

As used herein, a "nucleotide sequence" refers to a catenation of nucleotides by phosphodiester bridges.

As used herein, said "first nucleotide target sequence" refers to any nucleotide sequence of interest comprised by the at least one circular nucleic acid template, which is intended to be immobilized on said solid support, either as-such or directly, respectively, or in form of the complimentary nucleotide sequence.

As used herein, a "solid support" refers to any support comprising a surface which may be planar or curved and being capable of receiving and linking nucleic acid molecules. Solid supports of all kinds typically used in the field of immobilization of nucleic acid molecules are encompassed, such as planar chips, beads, capillaries etc. The support may be made of metal, glass, silica, plastics etc. It may also comprise a coated surface. The solid support may also comprise a soft and/or flexible surface.

As used herein, said "at least one first nucleic acid immobilized primer" and "at least one second nucleic acid immobilized primer" refer to oligonucleotide molecules which are linked to the surface of the solid support, either covalently or non-covalently. The first and second nucleic acid immobilized primers are preferably linked to the solid support via their 5' termini making their 3' termini available for a primer extension. The immobilized primers can be referred to as "anchor molecules" as the first immobilized primer anchors the circular nucleic acid template and the second immobilized primer anchors the first nucleic acid concatemeric amplification product to the solid support.

Said at least one first nucleic acid immobilized primer comprises a "second nucleotide sequence". The second nucleotide sequence is complementary to at least a segment of said first nucleotide target sequence comprised by said circular nucleic acid template allowing the annealing of the latter by a specific hybridization reaction to the first nucleic acid immobilized primer. Besides said second nucleotide sequence, the first nucleic acid immobilized primer may have other sequences. The first nucleic acid immobilized primer serves as the starting point for the synthesis of the first nucleic acid concatemeric amplification product.

Said at least one second nucleic acid immobilized primer comprises a "third nucleotide sequence". Said third nucleotide sequence is identical to at least a segment of said first nucleotide target sequence allowing the annealing of the first nucleic acid concatemeric amplification product by a specific hybridization reaction with the second nucleic acid immobilized primer due to the at least partial complementarity of said third nucleotide sequence and the fourth nucleotide sequence. The second nucleic acid immobilized primer serves as the starting point for the synthesis of the second nucleic acid concatemeric amplification product.

The second nucleotide sequence of the first nucleic acid immobilized primer is different from the third nucleotide sequence of the second nucleic acid immobilized primer.

As used herein, "a segment" of a nucleic acid molecule or a nucleotide sequence refers to a section of said molecule or sequence representing $\geq 10\%$, $\geq 15\%$, $\geq 20\%$, $\geq 25\%$, $\geq 30\%$, $\geq 35\%$, $\geq 40\%$, $\geq 45\%$, $\geq 50\%$, $\geq 60\%$, $\geq 70\%$, $\geq 80\%$, $\geq 90\%$, 100% of the length of the entire nucleic acid molecule, or $\geq 5$ nt, $\geq 10$ nt, $\geq 15$ nt, $\geq 20$ nt, $\geq 25$ nt, $\geq 30$ nt, $\geq 35$ nt, $\geq 40$ nt, $\geq 45$ nt, $\geq 50$ nt, $\geq 60$ nt, $\geq 70$ nt, $\geq 80$ nt, $\geq 90$ nt, $\geq 100$ nt of the nucleotide sequence.

As used herein, "partially complementary" means a nucleotide sequence which is sufficiently complementary to the referring sequence, thereby allowing a hybridization reaction between such sequences. Such partially complementary nucleotide sequences can be $\geq 50\%$, preferably $\geq 60\%$, more preferably $\geq 70\%$, more preferably $\geq 80\%$, more preferably $\geq 90\%$, more preferably $\geq 95\%$, more preferably $\geq 99\%$, or 100% complementary to each other.

As used herein, "strand displacement polymerase" refers to a nucleic acid or DNA polymerase with the ability to displace downstream DNA encountered during synthesis. Examples of strand displacement polymerases are φ29 DNA polymerase, Bst DNA polymerase, large fragment, deep Vent$_R$™ DNA polymerase, deep Vent$_R$™ (exo-) DNA polymerase, Klenow Fragment (3'→5' exo-), DNA polymerase I, large (Klenow) fragment, M-MuLV reverse transcriptase, Vent$_R$® DNA polymerase, Vent$_R$® (exo-) DNA polymerase, Bsu polymerase.

As used herein, "deoxynucleoside triphosphates (NTPs)" refer to a mixture of dNTPs such as a conventional mixture of the deoxynucleoside triphosphates dATP, dGTP, dCTP, dTTP, dITP, dUTP, including modified variants thereof, i.e. the building-blocks for the DNA polymerase to synthesize a new DNA strand.

As used herein, "reaction buffer" refers to such a buffer solution allowing the functioning of the strand displacement polymerase and, thus, the generation of the at least one first nucleic acid concatemeric amplification product.

As used herein, said "first nucleic acid concatemeric amplification product" refers to a nucleic acid molecule consisting of multiple copies of a "third nucleotide sequence" in a head-to-tail orientation. Said concatemeric amplification product is the result of the 'rolling circle amplification' (RCA). In the RCA the circular nucleic acid template rolls or rotates during the amplification reaction and thereby continuously serves as a template in the process of the primer extension until the rolling of the circle is stopped. As a result, the resulting amplification product is consisting of a plurality of third nucleotide sequences which are complimentary to the first nucleotide sequence of the circular nucleic acid template. In this context, "head-to-tail" orientation means that multiple copies of said third nucleotide sequences are linked to each other as follows: . . . 5'-3' 5'-3' 5'-3' 5'-3' 5'-3' . . . (→→). After a short RCA reaction period the rolling circle is stripped-off from the concatemeric amplification product by the strand displacement function of the strand displacement polymerase.

The hybridization reaction generally and in the method according to the invention requires conditions well-known to the skilled person depending on the temperature, the pH value, the salt conditions, the concentration of the nucleic acid molecules in the reaction mixture, there lengths, GC contents, nucleotide sequences etc.

"At least one", as used herein, refers to one entity at the minimum, e.g. one circular nucleic acid template, one nucleic acid non-immobilized primer, one primase etc. However, there can be more than one entity, e.g. two, three, four, five, six, seven, eight, nine, ten, one hundred, one thousand, ten thousand etc. entities.

Unless otherwise specified, the individual steps of the method according to the invention may be carried out sequentially or simultaneously/in parallel, respectively.

The method according to the invention has the advantage that the nucleic acid amplification product is consisting of a concatemer. As a result, the hybridization reaction of the first amplification product is very successful since—in contrast to only one sequence like in the cycle—the many sequences of the concatemer can hybridize with the nucleic acid immobilized primer. In addition, the first nucleic acid concatemeric amplification product can be anchored on the solid support—in comparison to the circular nucleic acid template—in a more efficient manner since the hybridization of a first copy of the third nucleotide sequence to a specific first nucleic acid immobilized primer is followed by the hybridization of a second, third, fourth copy of the third nucleotide to the neighboring first nucleic acid immobilized primers. Basically, the hybridization of the concatemeric amplification product comprising multiple copies of a nucleotide sequence is more successful than the hybridization of a nucleic acid molecule comprising only one of the copies of the nucleotide sequence by the factor representing the number of copies of this nucleotide sequence being present in the concatemeric amplification product.

The method according to the invention has the advantage that it does not only generate a two-dimensional spreading of the nucleic acid molecules on solid surfaces such as the methods known in the art. In the known methods the nucleic acid molecules are located on the surfaces individually and horizontally. In contrast, with the method according to the invention a three-dimensional spreading of the surface-immobilized nucleic acid molecules is achieved where the nucleic acid molecules are not only arranged on the surface horizontally but also vertically. This results in a higher density of amplified products per unit area.

Advantageously, the isothermal method according to the invention does not require an intervening denaturation step in the amplification, neither chemically nor thermally, as this is the case with non-isothermal methods in the art. This results in an acceleration of the hybridization proceedings.

Further advantageously, the method according to the invention results in an exponential amplification of the nucleic acid molecules directly on the surface of the solid support.

The method according to the invention comprises step (iii). Due to the fact that in this further step (iii) the first nucleic acid concatemeric amplification product represents a new nucleic acid template, the amplification mode changes from RCA to multiple displacement amplification (MDA). "Multiple displacement amplification" refers to a DNA amplification technique which can rapidly amplify minute amounts of the first nucleic acid concatemeric amplification product to a reasonable quantity for further use. The reaction starts by extending said second nucleic acid immobilized primer. DNA synthesis is carried out by a high fidelity enzyme, such as φ29 DNA polymerase, preferably at a constant temperature. Since the RCA is not been interrupted subsequent to the hybridization of the first nucleic acid concatemeric amplification product to said first nucleic acid immobilized primer, said at least one second nucleic acid concatemeric amplification product will be generated.

Said at least one second nucleic acid concatemeric amplification product comprises multiple copies of a "fifth nucleotide sequence" in a head-to-tail orientation. Said fifth nucleotide sequence is complementary to at least a segment of said fourth nucleotide sequence. As a consequence, said fifth nucleotide sequence corresponds—at least in parts—to said first nucleotide sequence of said circular nucleic acid template. Ultimately, via the second nucleic acid concatemeric amplification product the first nucleotide sequence of the circular nucleic acid template is immobilized to the solid support.

In an embodiment of the method according to the invention said at least one first nucleic acid immobilized primer and/or said at least one second nucleic acid immobilized primer comprise a cleavable linkage.

As used herein, "cleavable linkage" refers to an entity that can be cut or opened. If the first nucleic acid immobilized primer is provided with the cleavable linkage the opening thereof results in the release of the first nucleic acid concatemeric amplification product covalently attached thereto. If the second nucleic acid immobilized primer is provided with the cleavable linkage the opening thereof results in the release of the first nucleic acid concatemeric amplification product that is non-covalently hybridized thereto and/or, if applicable, the release of the second nucleic acid concatemeric amplification product that is covalently attached thereto.

The reaction mixture can be configured in a way that the cleavable linkage, optionally being present in any of both of the immobilized primers, can be but. For example, the temperature, the pH value or other reaction conditions such as the presence of a cleavage reagent or enzyme, can be adjusted in a way that simultaneously to the synthesis of the first nucleic acid concatemeric amplification product and/or the second nucleic acid concatemeric amplification product, if applicable, the opening of the cleavable linkage takes place. The inventors have surprisingly realized that the RCA process can still occur during the opening of the cleavable linkage, i.e. in the presence of the cleavage reagent or enzyme.

In another embodiment of the method according to the invention said cleavable linkage is a nucleotide, preferably a uracil, and further preferably after step (ii) an enzyme is added to the reaction mixture, said enzyme is capable of cleaving said cleavable linkage, wherein further preferably said enzyme is a DNA glycosylase, highly preferably a uracil-DNA glycosylase.

By this measure the cleavable linkage is realized in a simple but effective manner. In this embodiment DNA glycosylases having base excision activity are the enzymes of choice to open the cleavable linkage, in particular the uracil-DNA glycosylase if the nucleotide is a uracil. The inventors have surprisingly realized that the addition of an enzyme capable of cleaving said cleavable linkage to the reaction mixture in the course of the RCA also results in a reduction of secondary clusters unintentionally formed by the first nucleic acid concatemeric amplification product which may negatively influence any subsequent reaction such as massive parallel sequencing reactions.

In an embodiment the method according to the invention comprises the following further step:

iv) removing said at least one first nucleic acid concatemeric amplification product, preferably by denaturation.

By this measure a solid support is obtained which only comprises the at least one second nucleic acid concatemeric amplification product covalently linked to the at least one second nucleic acid immobilized primer. Such resulting solid support may be useful in any further molecular operation.

Preferably, the removal of said at least one first nucleic acid concatemeric amplification product is realized by the way of denaturation. The denaturation conditions are to be adjusted in a way that the first nucleic acid concatemeric amplification product can be washed from the solid surface together with the first nucleic acid immobilized primer. Now any desired further molecular operation involving the second nucleic acid concatemeric amplification product can be carried out. The second nucleic acid concatemeric amplification product is single stranded and comprises at least a segment of the first nucleotide sequence, i.e. the nucleotide sequence of the circular nucleic acid template in concatemeric form.

In another embodiment the method according to the invention comprises the following further step:

v) detection of said at least one first nucleic acid concatemeric amplification product and/or said at least one second nucleic acid concatemeric amplification product.

By this measure the individual concatemeric amplification products which are spread over the solid support or its surface in a point-like manner can be identified. The detection can be realized in different ways known to the skilled person, for example by a sequencing reaction, the use of hybridization probes etc.

In another embodiment of the method according to the invention said at least one first nucleic acid immobilized primer and/or said at least one second nucleic acid immobilized primer comprise an exonuclease protecting modification at their 3' termini, preferably a thioate bridge.

This measure increases the stability of the nucleic acid molecules against degradation by any exonuclease activity and, therefore, the effectivity of the entire method according to the invention.

In another embodiment of the method according to the invention said at least one circular nucleic acid template is a single stranded nucleic acid, preferably a single stranded DNA.

This measure has the advantage that no initiator protein is necessary which otherwise first has to nick one strand of the double stranded circular DNA molecule before the replication or amplification can begin.

In another embodiment of the method according to the invention said solid support comprises a material selected from the group consisting of: metal, glass, silica, plastics, and/or preferably is selected from the group consisting of: chips, beads, capillaries.

This measure has the advantage that the method according to the invention is adapted to any kind of material which is commonly used in molecular immobilization tasks.

Another subject matter of the present invention relates to the use of a combination of a first nucleic acid immobilized primer linked to a solid support and a second immobilized primer linked to said solid support in the method according to the invention, wherein preferably said first nucleic acid immobilized primer and/or said second immobilized primer comprise an exonuclease protecting modification at their 3' termini, further preferably a thioate bridge.

The features, characteristics, advantages and embodiments specified for the method according to the invention apply likewise to the use according to the invention.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention. The features mentioned in the specific embodiments are general features of the invention which are not only applicable in the specific embodiment but also in an isolated manner in the context of any embodiment of the invention.

The invention is now described and explained in further detail by referring to the following non-limiting examples and drawings.

Figure 2:
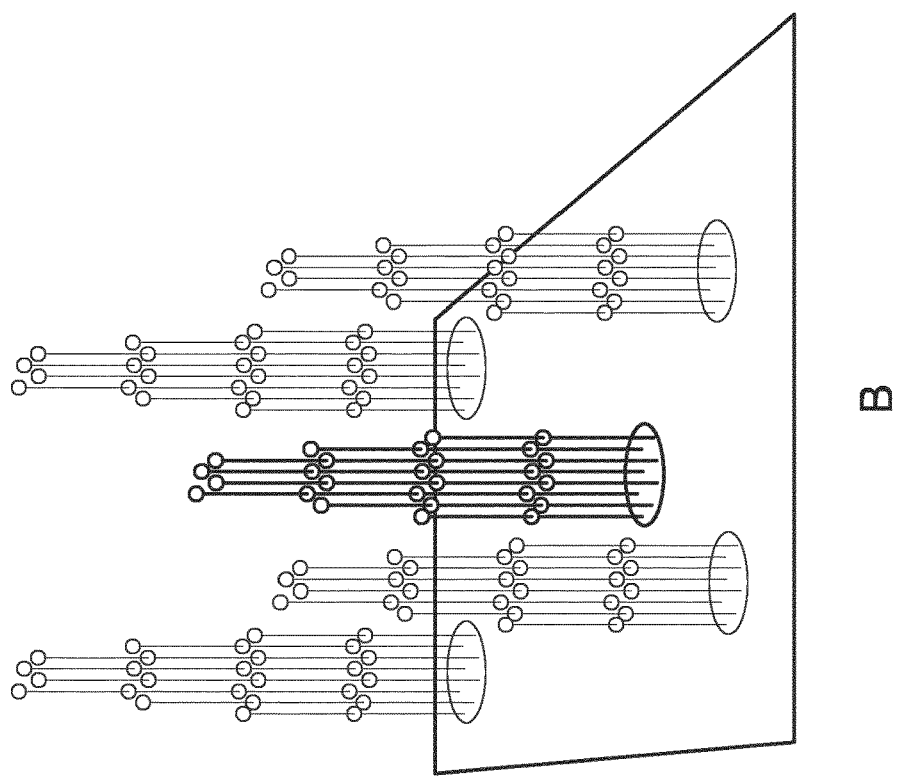
Figure 2:
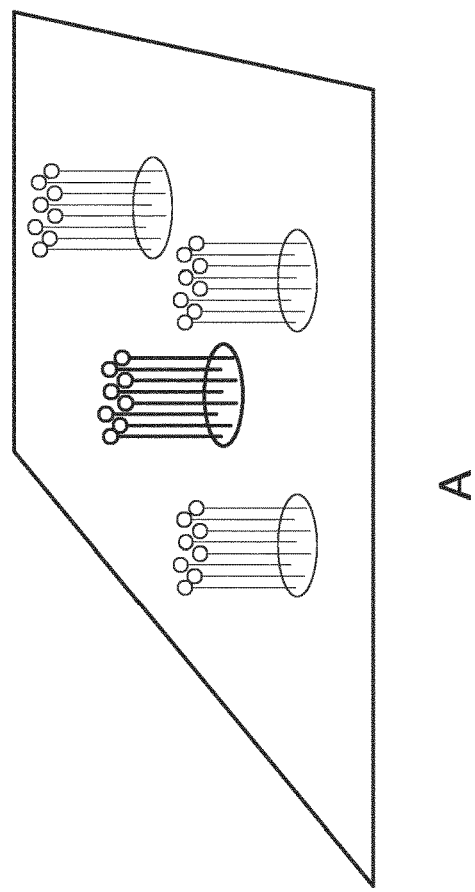
Figure 3:
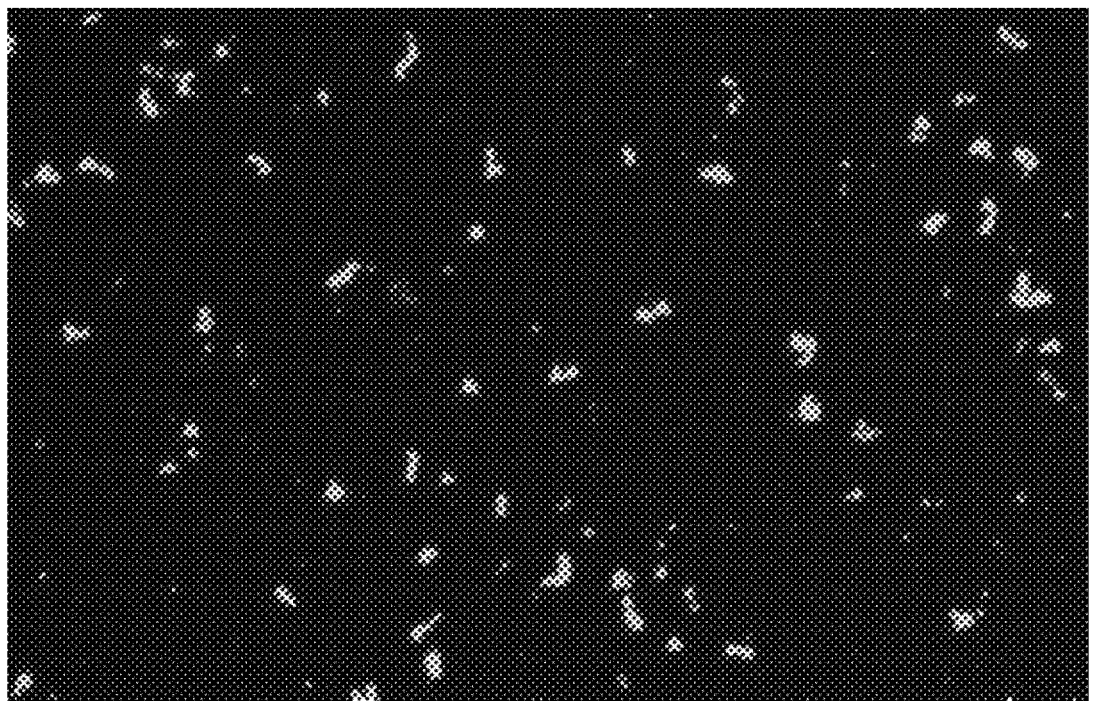
Figure 3:
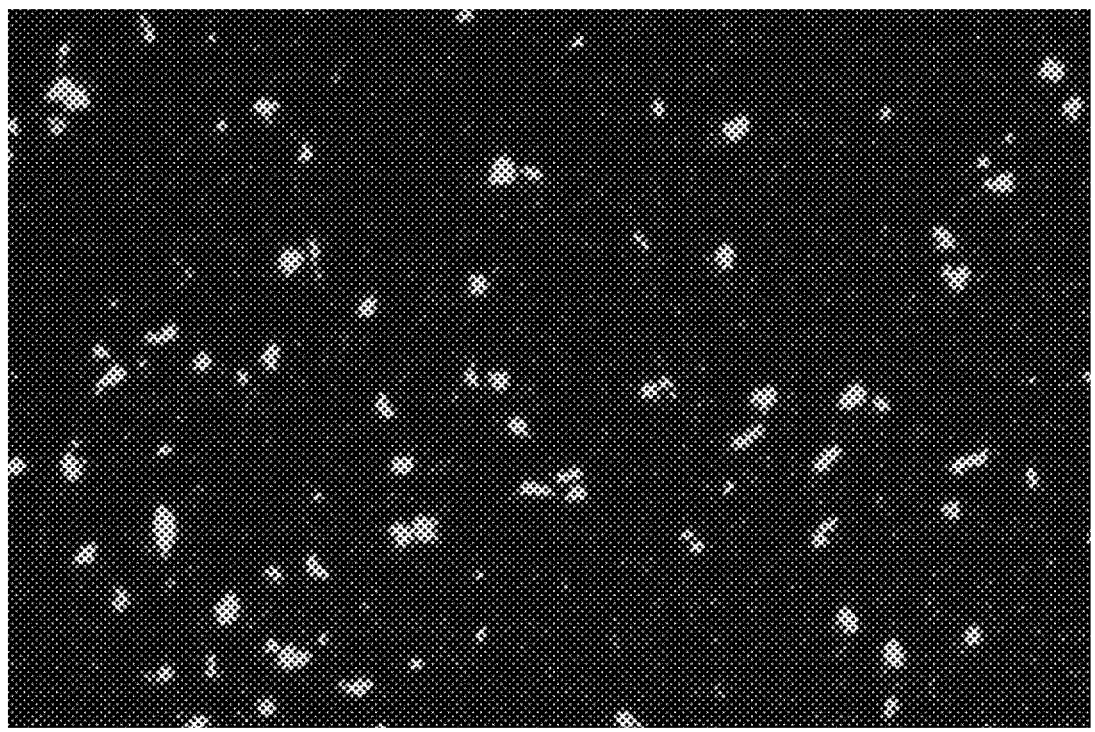

FIG. 1: shows a flow chart illustrating the method according to the invention (SEQ ID NOS: 16-19);

FIG. 2: shows the two-dimensional amplificate spreading in the art (A) versus three-dimensional amplificate spreading according to the invention (B). In the two-dimensional spreading the amplificate monomers are located next to each other. In the three-dimensional spreading the concatemeric amplificate monomers are also vertically arranged;

FIG. 3: shows the hybridization of the concatemeric amplification product (A) with and (B) without uracil-N-glycosylase.

EXAMPLES

1. Method According to the Invention

In FIG. 1 the individual steps of the method according to the invention are illustrated.

In step (i) the reaction mixture is provided comprising the circular nucleic acid template (1), in the following referred to as "circle", the solid support or surface (2) comprising the first (3) and second immobilized primers (4) linked to said support (2), the strand displacement polymerase (5) and, not shown, the dNTPs and the reaction buffer.

Optionally, the first (3) and/or second immobilized primer (4) may comprise a cleavable linkage (6a, 6b) which can be cut under specific conditions, such as the pH value, temperature, addition of reagents or enzymes etc. The solid surface (2) can be planar or curved, i.e. in principle any kind of surfaces can be used such as planar chips, beads, capillaries etc. The solid support and/or surface (2) can be made of different materials such as metal, glass, silica, plastics etc. In some cases a coating of the surface may be advisable.

In step (ii), sub-step 1, the circle (1) hybridizes to the first immobilized primer (3). The hybridization conditions such as temperature, pH value, circle concentration, primer concentration, salt conditions etc., depend on the length, the GC content and the nucleotide sequences of the both complementary sequences on the circle (1) and the primers (3, 4). It is shown that the first nucleotide sequence ($1^{st}$ nt seq.) of the circle (1) (circ.) is at least partially complementary to the second nucleotide sequence ($2^{nd}$ nt seq.) of the first immobilized primer (3) ($1^{st}$ imm. prim.).

Then, in sub-step 2, the rolling circle amplification begins. The first immobilized primer (3) is extended by the addition of dNTPs to its 3' terminus. The circle (1) "rolls" due to the strand displacement function of the polymerase (5), thereby exposing continuously its sequence which serves as a continuous template for the primer extension. This reaction results in a first concatemeric amplification product (7) comprising multiple copies of the same sequence in a head-to-tail orientation. It is shown that the first nucleotide sequence ($1^{st}$ nt seq.) of the circle (1) (circ.) is at least partially complementary to the fourth nucleotide sequence ($4^{th}$ nt seq.) of the first concatemeric amplification product (7) ($1^{st}$ concat.).

Optionally, the reaction mixture can be configured in such a manner that the cleavable linkage (6), optionally provided in any of both primers (3, 4), can be cut. For example, the temperature, pH value or other reaction conditions, such as the addition of a cleavable reagent or an enzyme, can be selected in a way that simultaneously with the synthesis of the concatemeric amplification product (7) the cleavage of the cleavable linkage (6) takes place. In doing so the reaction conditions may be chosen in a way that the cleavage happens step by step.

As shown, in sub-step 3 after a short RCA reaction period the first concatemeric amplification product (7) is peeled-off from the circle (1) via the strand displacement function of the polymerase (5) or the polymerase complex, respectively. The second immobilized primer (4) comprises a sequence allowing the hybridization to the first concatemeric amplification product (7). Since the first amplification product (7) is a concatemeric single stranded DNA molecule, the first amplification product (7) continuously comprises hybridization segments for the second immobilized primers (4). As a result, the first amplification product (7) folds towards the solid support (2) in the form of loops protruding away from its surface. It is shown that the fourth nucleotide sequence ($4^{th}$ nt seq.) of the first concatemeric amplification product (7) ($1^{st}$ concat.) is at least partially complementary to the third nucleotide sequence ($3^{rd}$ nt seq.) of the second immobilized primer (4) ($2^{nd}$ imm. prim.).

As shown in step (iii) the second immobilized primer (4) to which the first concatemeric amplification product (7) is hybridized, now serves as a primer in the multiple displacement amplification (MDA) in order to generate the second amplification product (8). The reactions in step (ii) are not necessarily interrupted after the hybridization of the first concatemeric amplification product (7) to the second immobilized primer (4) at the surface of the solid support (2). It is shown that the fourth nucleotide sequence of the first amplification product (7) is at least partially complementary to the fifth nucleotide sequence of the second amplification product (8).

The second amplification product (8) is also a concatemer consisting of multiple consecutively arranged copies of the same nucleotide sequence. This results in a localized, exponential MDA on the surface of the solid support (2).

In step (iv) it is shown that, optionally, after the MDA reaction the first concatemeric amplification product (7) can be denaturated and the cleavable linkage (6a) can be opened. The denaturation conditions can be adjusted in a manner that the first amplification product (7) together with the first immobilized primer (3) can be washed from the solid surface (2).

Now the reaction can follow which the operator intends to carry out with the exponentially amplified RCA products. These second concatemeric amplification product (8) is single stranded and the sequence information of the strand (second concatemeric amplification product (8): fifths nucleotide sequence corresponds to—at least in parts—to the first nucleotide sequence of the circle (1) in concatemeric form) is provided at the given location. The sequence information of the first concatemeric amplification (7) product is not provided at the given location.

In step (v) the detection of the second amplification product (8) is shown. By this, the individual concatemeric amplification products (8) can be detected which are spread over the surface of the solid support (2) in a spot-like manner. An exemplarily detection reaction is a sequencing reaction, a hybridization with sequence specific oligonucleotide probes (9) etc.

2. Experimental Validation 1

It should be demonstrated that circular DNA (circles) bound to a surface via immobilized primer molecules can be amplified by rolling circle amplification (RCA). As a control reaction mixtures without φ29 polymerase which is required for an RCA, is used.

Streptavidin plates (StreptaWell strips, Roche) provided with immobilized primer 1 for (sequence: biotin-aaa aaa aat tgc acc tat cct tgc gca gct cg*a*g; SEQ ID NO:1), primer 1 rev (sequence: biotin-aaa aaa aac cat gaa caa aat gtg act cat a*t*c; SEQ ID NO:2), and primer poly A (sequence: biotin-aaa aaa aa; SEQ ID NO:3) were incubated with different amounts of DNA circles (3.1 to 200 pg, sequence: atg acg ata tga gtc aca ttt tgt tca tgg gca tga cat tga tac aca gtt aga cga tag gac agt aca ttc gac cta tcc ttg cgc agc tcg aga tga cg; SEQ ID NO:4) in 50 μl of an appropriate buffer incubated for 50 min at room temperature (50 mM tris, pH 7.5; 10 mM MgCl$_2$, 100 mM NaCl, 0.0012% Tween 20). Then the supernatant is removed, washed and dissolved in 49 μl RCA reaction buffer (37 mM Tris pH 7.5; 50 mM KCl; 10 mM MgCl$_2$, 20 mM (NH$_4$)$_2$SO$_4$. 1 mM dNTP Mix). Phi29 DNA polymerase was added to a part of the reaction mixture. To the remaining part of the reaction mixture no polymerase was added. The reactions were carried out for 2 h at 38° C.

In the following the supernatant was removed and the surface was washed. The DNA was treated on the surface with 50 µl of denaturation lyses buffer (DLB, from the REPLI-g Mini Kit). After one 1 h at 37° C. the reaction was stopped with 50 µl of Stop Solution (from REPLI-g Mini Kit). The supernatant now contains DNA formally immobilized on the surface. This DNA can now be detected by a real time PCR (QuantiFast SYBR Green Kit) with appropriate primers [primer 2 forward: 5' ctg tgt atc aat gtc atg cc 3' (SEQ ID NO:5) and primer 2 reverse: 5' gtt aga cga tag gac agt aca 3' (SEQ ID NO:6)].

The position "*" in the oligonucleotides indicates that instead of a phosphate bridge a thioate bridge is provided between the sugar and the sugar phosphate backbone.

The result is shown in the following table 1.

TABLE 1

| | CT values measured after real-time PCT | |
|---|---|---|
| pg Circle | CT values RCA + ϕ29 pol | CT values RCA − ϕ29 pol |
| 200 | 9.2 | 22.6 |
| 100 | 10.0 | 23.8 |
| 50 | 11.3 | 25.1 |
| 25 | 12.6 | 25.9 |
| 12.5 | 14.7 | 27.1 |

The table clearly shows lower CT values in the mixes containing polymerase. Without polymerase the CT values are higher by 13.4 (+/−0.56) cycles corresponding to an amplification rate of approximately >10000 fold. This means, the sequence of the circles which were bound to the surface and amplified in the presence of ϕ29 polymerase were multiplied by the factor of ~10000.

3. Experimental Validation 2

The intention was to show that different RCA reaction times result in different amplification factors of the sequence of the circular DNA (circles). As a negative control reaction mixtures without circle were used to exclude any contamination.

Streptavidin plates (StreptaWell strips, Roche) provided with immobilized primer 1 for (SEQ ID NO:1), primer 1 rev (SEQ ID NO:2), and primer poly A (SEQ ID NO:3) were incubated for 15 min at room temperature in 50 µl of an appropriate buffer (50 Mm Tris, pH 7.5; 10 mM MgCl₂, 100 mM NaCl, 0.0012% Tween 20). In the following the supernatant was removed, the surface was washed and 50 µl of RCA reaction buffer (37 mM Tris pH 7.5; 50 mM KCl; 10 mM MgCl₂, 20 mM (NH₄)₂SO₄, 1 mM dNTP Mix; Phi29 DNA polymerase) was added. The reaction was carried out for 1 to 4 h at 38° C. Then the supernatant was removed and the surface was washed. Subsequently, the DNA was treated on the surface with 50 µl of DLB (from REPLI-g Mini Kit). After 1 h at 37° C. the reaction was stopped with 50 µl of Stop Solution (from REPLI-g Mini Kit). The supernatant now contains DNA formerly immobilized on the surface. This DNA can now be detected in a real-time PCR (QuantiFast SYBR Green Kit) with appropriate primers [primer 3 forward: 5' tgggcatgacattgatacacagttagac 3' (SEQ ID NO:7) and primer 3 reverse: 5' aaggataggtcgaatgtactgtcctatc 3' (SEQ ID NO:8)].

The result is shown in the following table 2

TABLE 2

| | CT values measured after real-time PCR | | |
|---|---|---|---|
| | +Circle | | −Circle |
| | CT values | CV | CT values |
| 1 h | 10.84 | 0.01 | 40.00 |
| 2 h | 9.52 | 0.01 | 40.00 |
| 3 h | 8.73 | 0.03 | 40.00 |
| 4 h | 7.75 | 0.03 | 40.00 |

The table shows lower CT values for longer RCA incubation times indicating a higher amplification factor for extended reaction times. After the first hour the CT value decreases each additional incubation hour by approximately 1 (+/−0.26) cycles.

4. Experimental Validation 3

It should be shown that by the use of oligonucleotides comprising uracil bases which were immobilized on a surface an RCA can be carried out in the presence of uracil-N-glycosylase.

Streptavidin coated glass slides provided with immobilized primer 1 for, primer 1 rev, and poly A were incubated for 15 min at room temperature in 15 µl of an appropriate buffer (50 mM Tris, pH 7.5; 19 mM MGCl₂, 137 mM NaCl, 0.0012% Tween 20). In the following non-hybridized circular DNA molecules were washed away. A rolling circle mixture comprising dNTPs and Phi29 polymerase and additional 2 U uracil-N-glycosylase were subjected to the surface and incubated for 2 h at 38° C. and then stopped at 65° C. In the following the surface was covered with a 1:10,000 YOYO®-1 iodide solution and incubated for the 30 min. After washing of the surface the glass slide was scanned.

The following mixtures were used:

Mixture 1: RCA mixture containing 2 U uracil-N-glycosylase

Mixture 2: RCA mixture not containing uracil-N-glycosylase

The result of the scanning is shown in FIG. 3 where partial figure (A) shows the mixture with uracil-N-glycosylase (UNG) and partial figure (B) shows the reaction mixture without UNG. It is clearly demonstrated that even in presence of UNG the RCA is still working very well. Surprisingly, the number of the many small spots which can form from side reactions is significantly reduced.

5. Experimental Validation 4

The intention was to show that the clusters generated during RCA can be used for sequencing reactions on the automated sequencer system GeneReader (QIAGEN).

Streptavidin coated GeneReader Flowcells provided with immobilized primer 1 for (sequence: 5"-Biotin-aa aaa aaa aaa aaa aaa aaa aaa uuc gac cua ucc uug cgc agc ucg*a*g) (SEQ ID NO:9), primer 1 rev (sequence: 5"-Biotin-aa aaa aaa aaa aaa aaa aaa aaa cca uga aca aaa ugu gac uca ua*u*c-3') (SEQ ID NO:10), and poly A (sequence: Biotin-aaa aaa aa) (SEQ ID NO:3) were incubated for 15 min at room temperature in 15 µl of an appropriate buffer (50 mM Tris, pH 7.5; 19 mM MgCl₂, 137 mM NaCl, 0.0012% Tween 20). In the following non-hybridized circular DNA molecules (sequence: atg acg ata tga gtc aca ttt tgt tca tgg gca tga cat tga tac aca gtt aga cga tag gac agt aca ttc gac cta tcc ttg cgc agc tcg aga tga cg) (SEQ ID NO:11) were washed away. A rolling circle mixture comprising dNTPs and Phi29 polymerase were subjected to the surface and incubated for 2 h at 38° C. and then stopped at 65° C. The surface was washed using a washing buffer (20 mM Tris-HCl, pH8.8; 50 mM KCl; 10 mM MgCl$_2$). In the following the surface was covered with a solution of hybridization buffer comprising 50 mM Tris-HCl pH8.8, 100 mM NaCl, 15 mM MgCl$_2$, and 1 µM sequencing primer (sequence: aggcatgtggttagacgataggacagtacattcgacctat) (SEQ ID NO:12). The incubation started at 90° C. and ramped down to 60° C. After aspiration of the hybridization solution, the surface was washed by 37.5 mM Tris-HCl, pH 7.5; 50 mM KCl; 10 mM MgCl$_2$; 20 mM (NH$_4$)$_2$SO$_4$ to eliminate non-hybridized sequencing primer. After this, the GeneReader Flowcell was used for sequencing for 20 cycles within the GeneReader Sequencing instrument using standard sequencing conditions.

The following sequence has been determined from the sequencing run: cct tgc gca gct cga gat ga (SEQ ID NO:13). The sequence correlates with the expected sequence. Therefore, sequencing using clusters generated by the RCA method described here is feasible.

6. Experimental Validation 5

The intention was to show that the clusters generated during RCA can be used for paired end sequencing reactions on the automated sequencer system GeneReader (QIAGEN).

The GeneReader Flowcell already used in experimental validation 4 was re-used for reverse sequencing. The GeneReader Flowcell was washed for 5 min at 75° C. using the washing buffer (20 mM Tris-HCl, pH8.8; 50 mM KCl; 10 mM MgCl$_2$; 50% DMSO). After aspiration of the washing buffer, the Flowcell ewas washed with washing buffer (37.5 mM Tris-HCl, pH 7.5; 50 mM KCl; 10 mM MgCl$_2$; 20 mM (NH$_4$)$_2$SO$_4$). Following the flowcell was used for hybridization of reverse sequencing primer (sequence: aggcatgtgctgtgtatcaatgtcatgcccatgaacaaa) (SEQ ID NO:14). For hybridization we assembled 1 µM reverse sequencing primer in 50 mM Tris-HCl pH8.8, 100 mM NaCl, 15 mM MgCl$_2$. After aspiration of the hybridization solution, the surface was washed by 37.5 mM Tris-HCl, pH 7.5; 50 mM KCl; 10 mM MgCl$_2$; 20 mM (NH$_4$)$_2$SO$_4$ to eliminate non-hybridized sequencing primer. After this, the GeneReader Flowcell was used for sequencing for 21 cycles within the GeneReader Sequencing instrument using standard sequencing conditions.

The following sequence has been determined from the sequencing run: atg tga ctc ata tcg tca tcg (SEQ ID NO:15). The sequence correlates with the expected sequence. Therefore, paired end sequencing using clusters generated by the RCA method described here is feasible.

Sequences

SEQ ID NO: 1
aaaaaaaatt gcacctatcc ttgcgcagct cgag

SEQ ID NO: 2
aaaaaaaacc atgaacaaaa tgtgactcat atc

SEQ ID NO: 3
aaaaaaaa

SEQ ID NO: 4
atgacgatat gagtcacatt ttgttcatgg gcatgacatt
gatacacagt tagacgatag gacag-tacat tcgacctatc
cttgcgcagc tcgagatgac g SEQ ID NO: 5
ctgtgtatca atgtcatgcc SEQ ID NO: 6
gttagacgat aggacagtac a SEQ ID NO: 7
tgggcatgac attgatacac agttagac SEQ ID NO: 8
aaggataggt cgaatgtact gtcctatc SEQ ID NO: 9
aaaaaaaaaa aaaaaaaaaa aaauucgacc uauccuugcg
cagcucg *a*g SEQ ID NO: 10
aaaaaaaaaa aaaaaaaaaa aaaccaugaa caaaauguga
cucaua *u *c SEQ ID NO: 11
atgacgatat gagtcacatt ttgttcatgg gcatgacatt
gatacacagt tagacgatag gacagtacat tcgacctatc
cttgcgcagc tcgagatgac g SEQ ID NO: 12
aggcatgtgg ttagacgata ggacagtaca ttcgacctat SEQ ID NO: 13
ccttgcgcag ctcgagatga SEQ ID NO:14
aggcatgtgc tgtgtatcaa tgtcatgccc atgaacaaa SEQ ID NO: 15
atgtgactca tatcgtcatc g

The invention claimed is:

1. A method for synthesizing at least one second nucleic acid concatemeric amplification product, comprising:
   i) providing a reaction mixture comprising:
      at least one circular nucleic acid template having a first nucleotide target sequence;
      a solid support comprising
         at least one first nucleic acid immobilized primer linked to said solid support and having a second nucleotide sequence being complementary to at least a segment of said first nucleotide target sequence, and
         at least one second nucleic acid immobilized primer linked to said solid support and having a third nucleotide sequence being identical to at least a segment of said first nucleotide target sequence;
      at least one strand displacement polymerase;
      deoxynucleoside triphosphates (dNTPs); and
      a reaction buffer;
   ii) incubating said reaction mixture under conditions allowing
      said at least one circular nucleic acid template to anneal to said at least one first nucleic acid immobilized primer;
      synthesizing at least one first nucleic acid concatemeric amplification product by extending said at least one first nucleic acid immobilized primer using rolling circle amplification (RCA), said at least one first nucleic acid concatemeric amplification product comprises multiple copies of a fourth nucleotide sequence in a head-to-tail orientation, said fourth nucleotide sequence being complementary to at least a segment of said third nucleotide sequence; and obtaining at least one first nucleic acid concatemeric amplification product-second nucleic acid immobilized primer complex immobilized to said solid support by annealing said at least one first nucleic acid concatemeric amplification product to said at least one second nucleic acid immobilized primer; and iii) synthesizing at least one second nucleic acid concatemeric amplification product by extending said second nucleic acid immobilized primer by multiple displacement amplification (MDA), said at least one second nucleic acid concatemeric amplification product comprises multiple copies of a fifth nucleotide sequence in a head-to-tail orientation, said fifth nucleotide sequence being complementary to at least a segment of said fourth nucleotide sequence.

2. The method of claim 1, wherein said at least one first nucleic acid immobilized primer and/or said at least one second nucleic acid immobilized primer comprise a cleavable linkage.

3. The method of claim 2, wherein said cleavable linkage is a nucleotide.

4. The method of claim 3, wherein said nucleotide is a uracil.

5. The method of claim 2, wherein after step (ii) an enzyme is added to the reaction mixture, and said enzyme is capable of cleaving said cleavable linkage.

6. The method of claim 5, wherein said cleavable linkage is a nucleotide, and said enzyme is a DNA glycosylase.

7. The method of claim 5, wherein said enzyme is a uracil-DNA glycosylase.

8. The method of claim 1, comprising the following further step:
iv) removing said at least one first nucleic acid concatemeric amplification product from the solid support.

9. The method of claim 1, comprising the following further step:
v) detection of said at least one first nucleic acid concatemeric amplification product and/or said at least one second nucleic acid concatemeric amplification product.

10. The method of claim 1, wherein said at least one first nucleic acid immobilized primer and/or said at least one second nucleic acid immobilized primer comprise an exonuclease protecting modification at their/its 3' termini/terminus.

11. The method of claim 10, wherein said exonuclease protecting modification is a thioate bridge.

12. The method of claim 1, wherein said at least one circular nucleic acid template is a single stranded nucleic acid.

13. The method of claim 1, wherein said solid support comprises a material selected from the group consisting of: metal, glass, silica, and plastics.

14. The method of claim 1, wherein said at least one circular nucleic acid template is a single stranded DNA.

15. The method of claim 1, wherein said solid support is selected from the group consisting of: a chip, a bead, and a capillary.

* * * * *